(12) United States Patent
Dittrich et al.

(10) Patent No.: US 7,317,120 B2
(45) Date of Patent: *Jan. 8, 2008

(54) PROCESS FOR THE PREPARATION OF 9,10-DIHYDRO-9-OXA-10-ORGANYLPHOSPHAPHENANTHRENE-10-OXIDE AND DERIVATIVES OF THE SAME SUBSTITUTED ON THE PHENYL GROUPS

(75) Inventors: Uwe Dittrich, Radebeul (DE); Berthold Just, Hamburg (DE); Manfred Döring, Wörth-Büchelberg (DE); Michael Ciesielski, Merseburg (DE)

(73) Assignee: Schill + Seilacher "Struktol" AG, Hamburg (DE)

( * ) Notice: Subject to any disclaimer, the term of this patent is extended or adjusted under 35 U.S.C. 154(b) by 344 days.

This patent is subject to a terminal disclaimer.

(21) Appl. No.: 10/918,838

(22) Filed: Aug. 13, 2004

(65) Prior Publication Data
US 2005/0038279 A1 Feb. 17, 2005

(30) Foreign Application Priority Data
Aug. 15, 2003 (DE) ................ 103 38 116

(51) Int. Cl.
*C07F 9/02* (2006.01)
(52) U.S. Cl. ...................................... 558/82
(58) Field of Classification Search ................ 558/81, 558/82
See application file for complete search history.

(56) References Cited

U.S. PATENT DOCUMENTS

| 3,702,878 A | 11/1972 | Saito et al. |
| 4,198,492 A | 4/1980 | Izawa et al. |
| 4,228,064 A | 10/1980 | Izawa et al. |
| 5,008,426 A | 4/1991 | Kleiner et al. |
| 5,096,935 A | 3/1992 | Kleiner et al. |
| 5,698,729 A | 12/1997 | Kleiner |
| 7,115,765 B2 * | 10/2006 | Sprenger et al. ............. 558/82 |

FOREIGN PATENT DOCUMENTS

| DE | 2 034 887 | 1/1972 |
| DE | 102 06 982 A | 9/2003 |
| EP | 0 304 782 | 3/1989 |
| EP | 0 787 738 | 8/1997 |
| EP | 0 806 429 | 11/1997 |
| EP | 1 279 719 | 1/2003 |
| JP | 57105451 | 6/1982 |
| JP | 57105456 | 6/1982 |
| JP | 63135396 | 6/1988 |
| JP | 11106619 | 4/1999 |
| JP | 2001270993 | 10/2001 |
| WO | WO 03/070736 | 8/2003 |

OTHER PUBLICATIONS

Chernyshev E A et al: "Organophosphorous Heterocyclic Compounds III. Synthesis . . . " Journal of General Chemistry of the USSR, Consultants Bureau, New York. Bd. 42, Jan. 1972, pp. 88-90.

* cited by examiner

Primary Examiner—Rei-tsang Shiao
(74) Attorney, Agent, or Firm—Collard & Roe, P.C.

(57) ABSTRACT

A process is provided for the preparation of 9,10-dihydro-9-oxa-10-organylphosphaphenanthrene-10-oxide and derivatives of same substituted on the phenyl groups, in which: (a) 9,10-dihydro-9-oxa-10-phosphaphenanthrene-10-oxide (DOP) or a derivative of same is reacted in the presence of at least one mono- or polyhydric alcohol with at least one ortho ester with formation of a first intermediate product, (b) the intermediate product from step (a) is optionally reacted with at least one further mono- or polyhydric alcohol with formation of a further intermediate product and (c) the intermediate product from steps (a) or (b) is transformed by addition of catalytic quantities of alkylation agent into 9,10-dihydro-9-oxa-10-organylphosphaphenanthrene-10-oxide or a derivative of same substituted on the phenyl groups.

27 Claims, No Drawings

PROCESS FOR THE PREPARATION OF 9,10-DIHYDRO-9-OXA-10-ORGANYLPHOSPHAPHENANTHRENE-10-OXIDE AND DERIVATIVES OF THE SAME SUBSTITUTED ON THE PHENYL GROUPS

CROSS REFERENCE TO RELATED APPLICATIONS

Applicants claim priority under 35 U.S.C. §119 of German Application No. 103 38 116.3 filed Aug. 15, 2003.

BACKGROUND OF THE INVENTION

1. Field of the Invention

The present invention relates to a new process for the preparation of 9,10-dihydro-9-oxa-10-organylphosphaphenanthrene-10-oxide and its derivatives substituted on the phenyl groups. The invention also relates to a process for the preparation of natural products and plastics with flame-retardant finishing using these derivatives.

2. The Prior Art

A process is known from the state of the art for the preparation of 9,10-dihydro-9-oxa-10-alkoxyphosphaphenanthrene-10-oxide and substituted derivatives of same by alcoholysis of 9,10-dihydro-9-oxa-10-halophosphaphenanthrene-10-oxide and its substituted derivatives in the presence of stoichiometric quantities of bases, such as tertiary amines or ammonia. See e.g. EP-A-0 787 738, EP-A-0 304 782 and also Phosphorus and Sulfur 1987, 31, page 71.

As alternative educts, but only for the preparation of 9,10-dihydro-9-oxa-10-aryloxyphosphaphenanthrene-10 derivatives, triphenyl phosphites or combinations of triphenyl phosphite/PCl₃ are disclosed in DE-A-20 34 887 or U.S. Pat. No. 3,702,878. These processes are however associated with the use of very high reaction temperatures of roughly 200° C. Furthermore transesterification reactions which can start from the said aryloxy derivatives are possible only with long-chained, low-volatility alcohols. 9,10-dihydro-9-oxa-10-organylphosphaphenanthrene-10-oxide derivatives can be obtained from the 9,10-dihydro-9-oxa-10-aryloxyphospha-phenanthrene derivatives by further reaction with stoichiometric quantities of organyl halides, preferably bromides and iodides, or in the case of phosphites also with stoichiometric quantities of alkylation agents that contain no halides. This therefore involves an application of the standard Michaelis-Arbuzov reaction (see Chem. Rev. 1981, 81, pages 415-430).

It is disclosed in Macromol. Rapid. Comm. 2001, 22, 1265-71 that 9-(9,10-dihydro-9-oxa-10-phosphaphenanthrene-10-oxide)-1-propene can be obtained by reacting 9,10-dihydro-9-oxa-10-phosphaphenanthrene-10-oxide (DOP) with methylene chloride and allyl bromide. The corresponding reaction with epichlorohydrin instead of allyl bromide, whereby 9-(9,10-dihydro-9-oxa-10-phosphaphenanthrene-10-oxide)-2-propene-1-ol can be obtained, is also disclosed.

Organic phosphorus compounds in which optionally substituted 9,10-dihydro-9-oxa-10-phosphaphenanthrene-10-oxide units are connected by bivalent hydrocarbon radicals which optionally contain heteroatoms or functional groups are known as flame-protection additives from JP-A-2001270993. Reference is made to JP-A-63135396 and 11106619 as regards the preparation of these phosphorus compounds. The abstract of JP-A-11106619 discloses that during preparation halogen-containing compounds such as 1,2-dichloroethane are used. The abstract of JP-A-63135396 discloses that the preparation takes place starting from a phosphinic acid derivative, which has an aromatic diol group, which is reacted with a glycidyl compound such as polyethylene glycol diglycidyl ether in solvent, preferably in the presence of a catalyst, e.g. Li, Mg, Cu or Fe, accompanied by heating.

Similar bridged phosphorus compounds as those disclosed in JP-A-2001270993 are disclosed in JP-A-57105456 and 57105451.

The abovementioned preparation of the 9,10-dihydro-9-oxa-10-alkyl-oxyphosphaphenanthrene derivatives by alcoholysis of the 9,10-dihydro-9-oxa-10-halophospha-phenanthrene derivatives (halogen e.g. chlorine) using bases (EP-A-0 787 738) requires a two-step prior preparation of the 10-halogen derivative with an unsatisfactory overall yield of less than 50%.

Preparation starting from the relatively expensive educt triphenyl phosphite or triphenyl phosphite/PCl₃ is also characterized by disadvantageous reaction conditions and a limited accessible product range, namely aromatic substituents only. In order to arrive at the desired end-products, such as 9,10-dihydro-9-oxa-10-organylphospha-phenanthrene-10-oxide and its substituted derivatives, further reaction steps must be carried out in each case using stoichiometric quantities of further reactants (transesterification, stoichiometric Michaelis-Arbuzov reaction). There are therefore in each case several (at least two to four) separate chemical reactions to be carried out, each accompanied by costly purification and separation operations.

A further disadvantage of the processes of the state of the art is that halogen-containing reactants must be used in stoichiometric quantities. Examples of this are the abovementioned standard Michaelis-Arbuzov reaction or the stoichiometric reaction with allyl bromide as described in Macromol. Rapid. Comm. 2001, 22, 1265-71.

On the other hand 9,10-dihydro-9-oxa-10-phosphaphenanthrene-10-oxide (DOP) is commercially available on an industrial scale and can be prepared in yields of over 95% in a one-step synthesis, see e.g. EP-A-0 806 429.

EP-A-1 279 719 describes flame-retardant fiber-treatment agents based on DOP derivatives. Alkyl, hydroxyalkyl, aralkyl, succinimide, hydroxy, alkoxy or aralkoxy groups are provided as substituents on the phosphorus. In U.S. Pat. No. 4,228,064 and U.S. Pat. No. 4,198,492 similar compounds are proposed for the preparation of polyphenyleneether resin compositions with flame-retardant finish.

SUMMARY OF THE INVENTION

The object of the present invention was thus to provide a process for the preparation of 9,10-dihydro-9-oxa-10-organylphosphaphenanthrene-10-oxide and derivatives thereof that are suitable for use as flame-retardant products, which avoids the abovementioned disadvantages of the state of the art. In particular the process should start from commercially easily available DOP or derivatives of same and deliver a synthesis path which is as easy and cost-favourable as possible and as halogen-free as possible.

These objects are achieved by the embodiments of the invention described hereinbelow.

The present invention thus provides a process for the preparation of 9,10-dihydro-9-oxa-10-organylphosphaphenanthrene-10-oxide and derivatives of same substituted on the phenyl groups in which:

(a) 9,10-dihydro-9-oxa-10-phosphaphenanthrene-10-oxide (DOP) or a derivative of same is reacted in the presence of at least one mono- or polyhydric alcohol with at least one ortho ester with formation of a first intermediate product, (b) the intermediate product from step (a) is optionally reacted with at least one further mono- or polyhydric alcohol with formation of a further intermediate product and (c) the intermediate product from step (a) or (b) is transformed by addition of catalytic quantities of alkylation agent into 9,10-dihydro-9-oxa-10-organylphosphaphenanthrene-10-oxide or a derivative of same substituted on the phenyl groups.

DETAILED DESCRIPTION OF PREFERRED EMBODIMENTS

By mono- or polyvalent molecular radicals, e.g. mono- or polyvalent hydrocarbon radicals, in this application is thus meant the bonding valency of these molecular radicals. As regards alcohols, valence is the number of OH groups of the alcohol. These can also be mono-, bi-, tri-, tetra- or polyfunctional, i.e. have different functional groups. See for example Römpp Chemie-Lexikon, $9^{th}$ edition, volume 1, 1989, page 106, "Alkohole" [Alcohols] entry; page 417, "Bindigkeit" [Covalence] or "Bindungswertigkeit" [Bonding Valency] entries. See also Fresenius, Görlitzer, *Organisch-chemische Nomenklatur*, Wissenschaftliche Verlagsgesellschaft mbH, Stuttgart 1989, pages 11, 28 to 32.

The process according to the invention has the advantage in particular that it can be carried out in the form of a one-pot synthesis, i.e. in a single reaction vessel, with excellent yields without costly purification operations between the reaction steps. The desired product is obtained in a purity of over 90% as measured by gas chromatography. In particular precision distillation to purify the product can be dispensed with.

The process according to the invention also has the advantage that, unlike the standard Michaelis-Arbuzov reaction, it can operate halogen-free, as halogen-free alkylation agents such as sulphuric acid or sulphonic ester are used in catalytic quantities.

The embodiment of the invention in which polyhydric alcohols are used makes possible the preparation of polyvalent ("bridged") derivatives which, when then used as flame-protection products, can be incorporated into polymer networks more advantageously than non-bridged derivatives and can have an improved flame-protection effect.

When carrying out the process halogen-free, hydrochloric acid is used at most as catalyst in the reaction steps (a) and/or (b). The hydrochloric acid can also be recovered within the framework of the removal of excess alcohol, as a result of which the incidence of halide waste is completely avoided.

When using acidic resins as catalysts the process can also be continuous. The continuous, multi-step reaction can be carried out in a reaction vessel, unlike the processes of the state of the art which in general require several separate, i.e. spatially separated, more costly reactions starting from educts some of which are unavailable industrially on a large scale.

Further catalysts that can be used according to the invention are organic sulphonic acids, e.g. p-toluenesulphonic acid which is a preferred catalyst.

DOP or a derivative of same according to Formula Ia or Ib

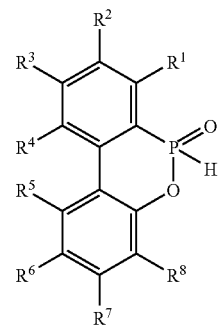

(Ia)

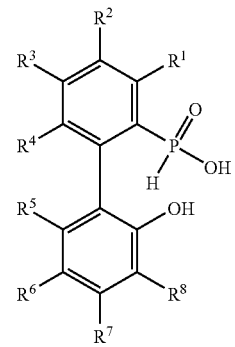

(Ib)

can thus be used as educt in step (a) of the process according to the invention in which $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more of the radicals $R^1$ to $R^8$ optionally being linked with formation of one or more cycles.

It may be pointed out that for the purposes of this application, compounds of Formula Ib are also called DOP derivatives although they do not have the (heteroatom-containing) basic phenanthrene framework, but are (substituted) o,o'-hydroxybiphenylphosphinic acids.

In Formulae Ia/b the radicals $R^1$ to $R^8$ independently of each other can have the following meanings:

Alkoxy: linear or branched alkyl groups with 1 to 30 carbon atoms (as named above) which are bound via an oxygen atom (—O—) to the framework, i.e. the 9,10-dihydro-9-oxa-10-phosphaphenanthrene-10-oxide structure.

Alkylthio: linear or branched alkyl groups with 1 to 30 carbon atoms (as named above) which are bound via a sulphur atom (—S—) to the skeleton.

Optionally substituted alkyl: saturated, linear or branched hydrocarbon radicals, in particular with 1 to 10 carbon atoms, e.g. $C_1$- to $C_6$ alkyl such as methyl, ethyl, propyl, 1-methyl ethyl, butyl, 1-methyl propyl, 2-methyl propyl, 1,1-dimethyl ethyl, pentyl, 1-methyl butyl, 2-methyl butyl, 3-methyl butyl, 2,2-dimethyl propyl, 1-ethyl propyl, hexyl, 1,1-dimethyl propyl, 1,2-dimethyl propyl, 1-methyl pentyl, 2-methyl pentyl, 3-methyl pentyl, 4-methyl pentyl, 1,1-dimethyl butyl, 1,2-dimethyl butyl, 1,3-dimethyl butyl, 2,2-dimethyl butyl, 2,3-dimethyl butyl, 3,3-dimethyl butyl, 1-ethyl butyl, 2-ethyl butyl, 1,3-trimethyl propyl, 1,2,2-trimethyl propyl, 1-ethyl-1-methyl propyl and 1-ethyl-2-methyl propyl.

Optionally substituted alkenyl: saturated, linear or branched hydrocarbon radicals, in particular with 2 to 10 hydrocarbon atoms and a double bond in any position, e.g. $C_2$- to $C_6$ alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 1,1,2-trimethyl-2-propenyl, 1-ethyl-1-methyl-2-propenyl, 1-ethyl-2-methyl-2-propenyl and 1-ethyl-2-methyl-2-propenyl.

Optionally substituted alkinyl: linear or branched hydrocarbon groups, in particular with 2 to 20 hydrocarbon atoms and a triple bond in any position, e.g. $C_2$- to $C_6$ alkinyl such as ethinyl, 1-propinyl, 2-propinyl, 1-butinyl, 2-butinyl, 3-butinyl, 1-methyl-2-propinyl, 1-pentinyl, 2-pentinyl, 3-pentinyl, 4-pentinyl, 1-methyl-2-butinyl, 1-methyl-3-butinyl, 2-methyl-3-butinyl, 3-methyl-1-butinyl, 1,1-dimethyl-2-propinyl, 1-ethyl-2-propinyl, 1-hexinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-1-pentinyl, 3-methyl-4-pentinyl, 4-methyl-1-pentinyl, 4-methyl-2-pentinyl, 1,1-dimethyl-2-butinyl, 1,1-dimethyl-3-butinyl, 1,2-dimethyl-3-butinyl, 2,2-dimethyl-3-butinyl, 3,3-dimethyl-1-butinyl, 1-ethyl-2-butinyl, 1-ethyl-3-butinyl, 2-ethyl-3-butinyl and 1-ethyl-1-methyl-2-propinyl.

An optionally substituted, saturated or a once- or twice-unsaturated ring which along with carbon atoms can contain one to three of the following heteroatoms as ring members: oxygen, sulphur and nitrogen, for example carbocycles such as cyclopropyl, cyclopentyl, cyclohexyl, cyclopent-2-enyl, cyclohex-2-enyl, 5- to 6-membered, saturated or unsaturated heterocycles, containing one to three nitrogen atoms and/or an oxygen or sulphur atom such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxaolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl.

An optionally substituted one- or two-core aromatic ring system which along with carbon atoms can contain one to four nitrogen atoms or one or two nitrogen atoms and one oxygen or sulphur atom or one oxygen or sulphur atom as ring members: i.e. aryl radicals such as phenyl and naphthyl, preferably phenyl or 1- or 2-naphthyl, and hetaryl radicals, for example 5-ring heteroaromatics containing one to three nitrogen atoms and/or one oxygen or sulphur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 5-tetrazolyl, 1,2,3,4-thiatriazole and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl.

Six-ring heteroaromatics containing one to four nitrogen atoms as heteroatoms such as 2-pyridinyl, 3-pyridinyl, 4-pyridinyl, 3-pyradazinyl, 4-pyradazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyrazinyl.

The addition "optionally substituted" in relation to alkyl, alkenyl and alkinyl groups is intended to express that these groups can be partially or completely halogenated (i.e. the hydrogen atoms of these groups can be partially or completely replaced by the same or different halogen atoms as named above (preferably fluorine, chorine and bromine, in particular fluorine and chlorine) and/or can carry one to three, in particular one of the following radicals:

Nitro, cyano, $C_1$- to $C_4$ alkoxy, $C_1$- to $C_4$ alkoxycarbonyl or an optionally substituted one- or two-core aromatic ring system which along with carbon atoms can contain one to four nitrogen atoms or one or two nitrogen atoms and one oxygen or sulphur atom or one oxygen or sulphur atom as ring members, i.e. aryl radicals such as phenyl and naphthyl, preferably phenyl or 1- or 2-naphthyl, and hetaryl radicals, for example 5-ring heteroaromatics containing one to three nitrogen atoms and/or an oxygen or sulphur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 5-tetrazolyl, 1,2,3,4-thiatriazole and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl.

Furthermore the substituents can be six-ring heteroaromatics containing one to four nitrogen atoms as heteroatoms such as 2-pyridinyl, 3-pyridinyl, 4-pyridinyl, 3-pyradazinyl, 4-pyradazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyrazinyl.

The addition "optionally substituted" in relation to the cyclic (saturated, unsaturated or aromatic) groups is intended to express that these groups can be partially or completely halogenated (i.e. the hydrogen atoms of these groups can be partially or completely replaced by the same or different halogen atoms as mentioned above (preferably fluorine, chlorine and bromine, in particular fluorine and chlorine) and/or can carry one to three, preferably one of the following radicals: nitro, cyano, $C_1$- to $C_4$ alkyl, $C_1$- to $C_4$ alkoxy and $C_1$- to $C_4$ alkoxycarbonyl.

The one- or two-core aromatic or heteroaromatic systems mentioned in the case of the radicals can for their part be partially or completely halogenated, i.e. the hydrogen atoms of these groups can be partially or completely replaced by halogen atoms such as fluorine, chlorine, bromine and iodine, preferably fluorine and chlorine.

These one- or two-core aromatic or heteroaromatic systems can, along with the named halogen atoms, carry in addition one to three of the following substituents:

Nitro, cyano, thiocyanato;
Alkyl, in particular $C_1$- to $C_6$ alkyl as named above,
$C_1$- to $C_{30}$ alkoxy,
$C_1$- to $C_{30}$ alkylthio,
$C_1$- to $C_4$ alkylamino,
$C_1$- to $C_6$ alkylcarbonyl,
$C_1$ to $C_6$ alkoxycarbonyl,
$C_1$- to $C_6$ alkylaminocarbonyl,
$C_1$- to $C_6$ alkylcarboxyl,
$C_1$- to $C_6$ alkylcarbonylamino,
$C_3$- to $C_7$ cycloalkyl such as cyclopropyl, cyclobutyl, cyclopentyl, cyclohexyl and cycloheptyl, preferably cyclopropyl, cyclopentyl and cyclohexyl, in particular cyclopropyl;
$C_3$- to $C_7$ cycloalkoxy such as cyclopropyloxy, cyclobutyloxy, cyclopentyloxy, cyclohexyloxy and cycloheptyloxy, preferably cyclopentyloxy and cyclohexyloxy, in particular cyclohexyloxy;
$C_3$- to $C_7$ cycloalkylthio such as cyclopropylthio, cyclobutylthio, cyclopentylthio, cyclohexylthio and cycloheptylthio, preferably cyclohexylthio;
$C_3$- to $C_7$ cycloalkylamino such as cyclopropylamino, cyclobutylamino, cyclopentylamino, cyclohexylamino and cycloheptylamino, preferably cyclopropylamino and cyclohexylamino, in particular cyclopropylamino;
further radicals for optionally substituted one- or two-core aromatic or heteroaromatic radicals:
Alkenyl, alkinyl, haloalkenyl, haloalkinyl, alkenyloxy, alkinyloxy, haloalkenyloxy, haloalkinyloxy, alkenylthio, alkinylthio, alkylsulphoxy, alkylsulphonyl, alkenylsulphoxy, alkinylsulphoxy, alkinylsulphonyl.

Although the radicals $R^1$ to $R^8$ can be halogens, such as fluorine, chlorine, bromine or iodine, preferably chlorine or bromine, derivatives are preferred in which none of the radicals $R^1$ to $R^8$ is a halogen atom. Accordingly, derivatives are preferred in which none of the radicals $R^1$ to $R^{11}$ contains halogen atoms, $R^9$ to $R^{11}$ being defined as follows. Halogen-free derivatives are therefore preferred according to the invention.

Although a substitution pattern is possible in which all the radicals $R^1$, $R^2$, $R^3$ and $R^4$ independently of each other are a halogen atom or a hydrocarbon group, a preferred version relates to the case that, of the radicals $R^1$, $R^2$, $R^3$ and $R^4$, at least two, preferably at least three are hydrogen atoms, in particular $R^1$, $R^2$, $R^3$ and $R^4$ are all hydrogen atoms.

Although a substitution pattern is possible in which all the radicals $R^5$, $R^6$, $R^7$ and $R^8$ independently of each other are a halogen atom or a hydrocarbon group, a preferred version relates to the case that, of the radicals $R^5$, $R^6$, $R^7$ and $R^8$, at least two, preferably at least three are hydrogen atoms, and in particular $R^5$, $R^6$, $R^7$ and $R^8$ are all hydrogen atoms.

Substitution patterns at the aromatic ring systems are preferred in which in each case two of the radicals $R^1$, $R^2$, $R^3$ and $R^4$ and of the radicals $R^5$, $R^6$, $R^7$ and $R^8$ are a halogen atom or a hydrocarbon group, more preferably only one of the radicals $R^1$, $R^2$, $R^3$ and $R^4$ and of the radicals $R^5$, $R^6$, $R^7$ and $R^8$ in each case being a halogen atom or a hydrocarbon group and in particular all the radicals $R^1$ to $R^8$ being hydrogen atoms.

For the preferred embodiments described in the previous paragraph $C_1$- to $C_6$ alkyl groups are preferred as hydrocarbon groups. If the hydrocarbon groups contain a heteroatom, $C_1$- to $C_6$ alkoxy groups are the preferred radicals for these versions. The heteroatom is thus then oxygen.

In step (a) of the reaction according to the invention DOP or a derivative of same, in particular a derivative according to the above Formula Ia or Ib, is therefore reacted in the presence of at least a mono- or polyhydric alcohol with at least one ortho ester, a first intermediate product forming.

An ortho ester of Formula II $$R^9C(OR^{10})_3 \tag{II}$$

in which $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, is preferably used in step (a).

An alcohol of Formula IIIa $$R^{11}(OH)_y \tag{IIIa}$$

in which $R^{11}$ is a mono- or polyvalent hydrocarbon group which optionally contains one or more heteroatoms selected from oxygen, nitrogen, sulphur, phosphorus, silicon and halogen, and y is 1 to 10, preferably 1 to 4, in particular 1, 2, 3 or 4, is preferably used in step (a).

In a preferred embodiment R9 is a hydrogen atom, an alkyl or an aryl group, the definitions of terms relating to the radicals $R^1$ to $R^8$ applying accordingly and a hydrogen atom or a methyl group are particularly preferred.

Preferred radicals $R^{10}$ and $R^{11}$ independently of each other are selected from alkyl, alkenyl, alkinyl, aryl and glycidyl groups, the definitions of terms relating to the radicals $R^1$ to $R^8$ applying accordingly, and methyl, ethyl and allyl are particularly preferred. In a further preferred version the radicals $R^{10}$ and $R^{11}$ are the same. Further examples of the radicals $R^{10}$ and $R^{11}$ are the optionally substituted alkyl, alkenyl and alkinyl radicals listed above in relation to the definitions of $R^1$ to $R^8$ as well as the above-mentioned, optionally substituted, saturated or once- or twice-unsaturated rings.

Orthoformic acid esters, in particular trimethyl orthoformate, triethyl orthoformate or triallyl orthoformate are preferred as ortho esters. However, ortho esters in which the radicals $R^{10}$ are different can also be used.

Methanol, ethanol, propanol, isopropanol and butanol are preferred in particular as alcohols. Diols, glycols, polyglycols, tri- and tetrahydric alcohols, e.g. ethylene glycol, glycerol and pentaerythritol are preferred as polyhydric alcohols.

Further examples of bi-, tri- or tetrahydric alcohols are listed below.

Examples of bivalent radicals in alcohols of Formula $R^{11}(OH)_2$ are:

$(CH_2)_n$, $(CH_2)_nO(CH_2)_m$, $(CH_2)_nNR(CH_2)_m$, $(CH_2)_nN(COR)(CH_2)_m$, $(CH_2)_nS(CH_2)_m$, $OPR(OCH_2CH_2)_2$, $(CH_2)_nOOC\text{\textasciitilde}\text{\textasciitilde}COO(CH_2)_m$, $(CH_2)_nX\text{\textasciitilde}\text{\textasciitilde}X(CH_2)_m$,

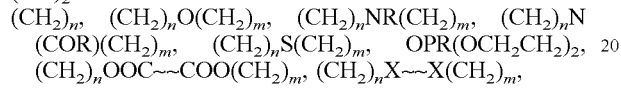

with $X=(CR_2)_m$, $SO_2$, SO, S, O, NR, OPR and R=H or alkyl and (COR)=acyl; ~~=aliphatic, cycloaliphatic or aromatic bridges; m,n are each integers and 1 or larger, preferably 1 to 10, 1 to 5 or 1 to 3, e.g. 2 or 4.

Examples of trivalent radicals in alcohols of Formula $R^{11}(OH)_3$ are:

$RC(CH_2)_l(CH_2)_m(CH_2)_n$
$RSi(OCH_2CH_2)_3$
$B(OCH_2CH_2)_3$
$O=P(CH_2CH_2)_3$
$OP(OCH_2CH_2)_3$
$N(CH_2)_l(CH_2)_m(CH_2)_n$
$M(COO(CH_2)_l)(COO(CH_2)_m)(COO(CH_2)_n)$
ethers of trihydric alcohols, e.g. triethers of glycerol or 1,1,1-tris(hydroxymethyl)propane

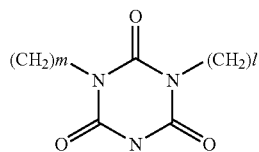

R, m, n being defined as above for the bivalent radicals and 1 being defined as m and n and M being a trivalent hydrocarbon radical and the ester groups being arranged at the same or different C atoms.

Examples of tetravalent radicals in alcohols of Formula $R^{11}(OH)_4$ are:

$C(CH_2)_l(CH_2)_m(CH_2)_n(CH2)_o$
$Si(OCH_2CH_2)_4$
$M'(COO(CH_2)_l)(COO(CH_2)_m)(COO(CH2)_n)(COO(CH_2)_o)$ $(CH_2)_n(CH_2)_oNOC\text{\textasciitilde}\text{\textasciitilde}CON(CH_2)_l(CH_2)_m$,
$(CH_2)_n(CH_2)_oN\text{---}\text{\textasciitilde}\text{---}N(CH_2)_l(CH_2)_m$, ~~R, l, m, n being defined as above for the trivalent radicals and o being defined as l, m, n and M' being a tetravalent hydrocarbon radical and the ester groups being arranged at the same or different C atoms.

The intermediate product obtained in step (a) according to the preferred versions described above of the invention can be described by the following Formula IVa or IVb:

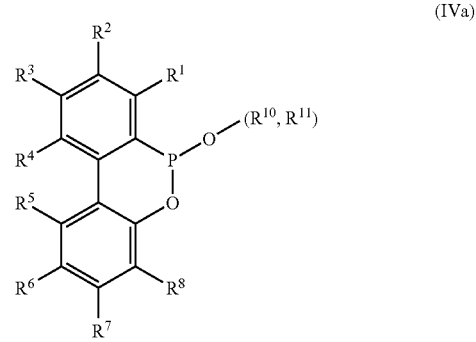

(IVa)

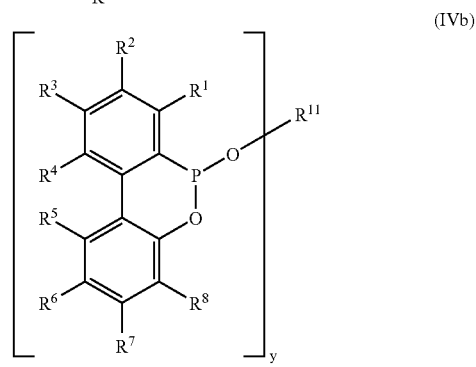

(IVb)

in which the radicals $R^1$ to $R^{11}$ and y have the meanings given above.

Reaction step (a) can be carried out according to the invention without further solvents. If a solvent is used, this can be benzene, alkylated benzenes, aliphatic or cycloaliphatic ethers. In general the reaction is carried out at temperatures of −20° C. to 120° C., preferably 0° C. to 100° C., in particular 5° C. to 8° C. Reaction step (a) can be carried out under normal pressure or slight excess pressure.

In particular if the formation of product mixtures is to be avoided, according to the invention the intermediate product from step (a) can be reacted in reaction step (b) with at least one further mono- or polyhydric alcohol with formation of a further intermediate product. The alcohol used preferably has the Formula IIIb $$R^{12}(OH)_y, \quad \text{(IIIb)},$$

in which $R^{12}$ is a mono- or polyvalent hydrocarbon group which optionally contains one or more heteroatoms selected from oxygen, nitrogen, sulphur, phosphorus, silicon and halogen, and y is 1 to 10, preferably 1 to 4, in particular 1, 2, 3 or 4, and the alcohol is different from that used in step (a).

With regard to preferred radicals $R^{12}$, reference is made to the above definitions of $R^{11}$. These also apply to $R^{12}$.

In particular the following embodiments of the process according to the invention are possible:

A monohydric alcohol (y=1) is used in both step (a) and step (b).

A monohydric alcohol (y=1) is used in step (a) and a polyhydric alcohol (y=2 to 4) is used in step (b).

A polyhydric alcohol (y=2 to 4) is used in both step (a) and step (b).

A polyhydric alcohol (y=2 to 4) is used in step (a) whereas a monohydric alcohol (y=1) is used in step (b).

The reaction with at least one further alcohol in step (b) of the process according to the invention has the advantage that price-favourable ortho esters can be used in step (a), which leads to a product mixture if $R^{10}$ is not the same as $R^{10}$. If desired, a uniform product can then be obtained by transesterification with a further alcohol in step (b).

The reaction steps (a) and (b) are preferably carried out in the presence of catalysts. These can be Lewis acids or Br"nsted acids, for example. Hydrogen halides, phosphoric acids, sulphuric acids, in particular organic sulphonic acids and similar are suitable in particular. Hydrochloric acid or p-toluenesulphonic acid is particularly preferred. The catalyst or catalysts are preferably recovered.

The products obtained according to step (b) can be described by Formula Va or Vb

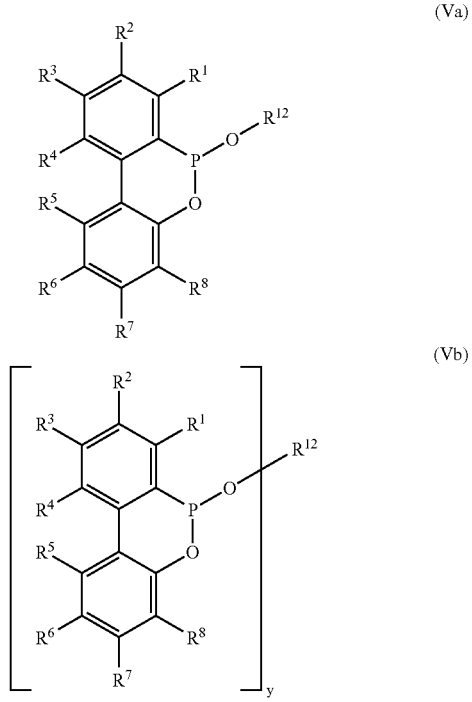

(Va)

(Vb)

in which the radicals $R^1$ to $R^{12}$ have the meanings given above.

After the reactions (a) and/or (b) have ended, excess alcohol and also volatile educts (ortho esters) are distilled off, e.g. with the help of a rotary evaporator. The undistilled residue, i.e. the products according to Formula IVa or IVb and Va or Vb respectively, can then be intramolecularly rearranged solvent-free accompanied by addition of catalytic quantities of alkylation agents, which preferably takes place at increased temperatures of over 100 C and under normal pressure. If desired, one or more solvents can also be added, e.g. xylenes, DMF (dimethylformamide) or NMP (N-methylpyrrolidone).

In step (c) of the process according to the invention halogen-free alkylation agent(s) is added in catalytic quantities of in particular 0.1-100 mmol/mol to the intermediate product of step (a) or (b), in the presence of which the intermediate product which is trivalent relative to phosphorus changes into a pentavalent phosphorus compound. Alkyl sulphates, alkyl sulphonates, alkyl-p-toluenesulphonates, alkyl sulphinates, alkyl fluoroborates, alkyl trifluoromethane sulphonates, trialkyl oxonium salts, alkyl maleimides, lactones, lactames, sulphones, salts of Mannich bases and carboxylic anhydrides are used as alkylation agents. Alkyl sulphonates of aromatic sulphonic acids such as alkyl-p-tolylsulphonates, e.g. ethyl p-toluenesulphonates, or alkyl sulphates such as dimethyl sulphate are preferred.

After the catalytic conversion in step (c) volatile constituents are optionally removed, in general by distillation, optionally under reduced pressure or vacuum, and the product thus obtained. As a final purification step, washing with water or a mixture of water and acid can take place in order to thus remove catalyst residues and possibly unreacted educt (DOP). The obtained purity of the product is such that it can be used immediately in technical applications such as flame-protection products without further purification or working-up steps being necessary.

The products obtained using the preferred reaction components described above can be described by Formula VIa or VIb

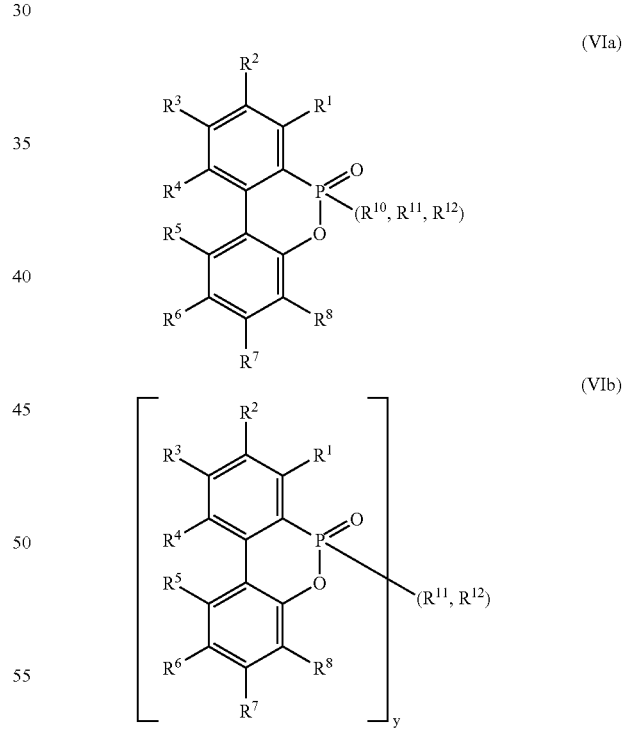

(VIa)

(VIb)

$R^1$ to $R^{12}$ and y having the meanings given above. The radicals $R^1$ to $R^8$ are preferably hydrogen, the radical $R^{10}$ methyl or ethyl and the radicals $R^{11}$ or $R^{12}$ methyl, methylene, methanetriyl or methanetetrayl, ethyl, ethylene, ethanetriyl or ethanetetrayl.

The notation ($R^{10}$, $R^{11}$) or ($R^{10}$, $R^{11}$, $R^{12}$) or ($R^{11}$, $R^{12}$) in Formulae Va/b and VIa/b is an abbreviated notation for several alternatives in which one of each of the radicals listed in the expressions in brackets is present, whereas the other radicals are not present.

The invention also relates to a process for the preparation of natural products and plastics with flame-retardant finishing in which one or more derivatives according to the invention are added to a natural product or plastic.

The process is characterized in that 9,10-dihydro-9-oxa-10-organylphosphaphenanthrene-10-oxide or derivatives of same substituted on the phenyl groups are firstly prepared as intermediate products according to the above process, and these intermediate products are then introduced into the natural product or plastic.

The intermediate products can be introduced into the natural product or plastic by addition or reaction. In particular with the DOP derivatives prepared using polyhydric alcohols, reactive incorporation, i.e. binding into the natural product or plastic using a chemical reaction, is an advantageous variant.

Alternatively one or more of the derivatives prepared according to the invention can be added to an uncured natural product or plastic (synthetic resin), and the mixture of uncured natural product or plastic and derivative according to the invention can then be cured to form a cured natural product or plastic with flame-retardant finishing.

Plastics are preferably selected from the group composed of polyester, polyamide, polycarbonate, polystyrene, polyethylene, polypropylene, phenolic and epoxy resins. Preferred natural products are cotton, wool, linen and hemp.

A flameproof epoxy resin prepared according to the invention preferably contains 2 to 7 wt.-% phosphorus in the resinous matter. By "resinous matter" is meant only the overall weight of epoxy resin used and derivative according to the invention of Formula VI a/b. Further optionally used components such as curing agents, fillers or glass-fiber mat are not taken into account in this determination of the phosphorus content. An advantage of the epoxy resin with flameproof finishing according to the invention is that it can be prepared using a reactive derivative (e.g. $R^{10}$ and/or $R^{11}$ equalling allyl or glycidyl). At least a part of the reactive derivative of Formula I then reacts with the epoxy resin and/or the optionally used curing agent. It is preferred according to the invention that at least 50 wt.-% of the phosphorus content is chemically bound into the epoxy resin.

Preferred embodiments and advantages of the present invention result in particular from the examples.

The following Examples 1 to 4 illustrate reaction step (a) of the process according to the invention:

EXAMPLE 1

9,10-dihydro-9-oxa-10-methoxyphosphaphenanthrene (6-methoxy-(6H)-dibenz [c,e][1,2]-oxaphosphorine) from DOP and Trimethyl Orthoformate in Methanol 1.33 mol (287.5 g) DOP and 2.5 ml conc. HCl are dissolved in 1230 ml methanol and the mixture heated to 85 C to reflux (slight excess pressure). After 45 mins a further 0.5 ml conc. HCl are added and 2.7 mol (295 ml) trimethyl orthoformate then added dropwise within 5 h. During the dropwise addition of the trimethyl orthoformate 0.5 ml conc. HCl are added every 30 mins. After the reaction has ended, all volatile constituents are removed on the rotary vaporator under reduced pressure. The yellow, oily residue is distilled in fine vacuum (0.1 mbar). At 130 to 155° C. the product distils as a colourless, oily liquid which solidifies slowly after several weeks. Yield: 265 g, 87% of theory.

EXAMPLE 2

9,10-dihydro-9-oxa-10-ethoxyphosphaphenanthrene (6-ethoxy-(6H)-dibenz [c,e][1,2]-oxaphosphorine) from DOP, Ethanol and Trimethyl Orthoformate 0.2 mol (43.2 g) DOP and 0.5 ml conc. HCl are dissolved in 352 ml ethanol and the mixture heated to 90° C. to reflux (slight excess pressure). After 50 mins a further 0.1 ml conc. HCl are added and 0.4 mol (59.3 g, 66.5 ml) trimethyl orthoformate then added dropwise within 4 h. During the dropwise addition of the trimethyl orthoformate 0.1 ml conc. HCl are added every 30 mins. After the reaction has ended, all volatile constituents are removed on the rotary vaporator under reduced pressure. The yellow, oily residue is distilled in fine vacuum (0.1 mbar). At 135 to 142° C. the product distils as a colourless, oily liquid (solidified melt Fp=42 C). Yield: 44.8 g, 92% of theory.

EXAMPLE 3

9,10-dihydro-9-oxa-10-ethoxyphosphaphenanthrene (6-ethoxy-(6H)-dibenz [c,e][1,2]-oxaphosphorine) from DOP, Ethanol and Trimethyl Orthoformate 5.0 mol (1081 g) DOP and 2.0 ml conc. HCl are dissolved in 4400 ml ethanol and the mixture heated to 95° C. to reflux (slight excess pressure). After 1 h a further 1.0 ml conc. HCl are added and 6.5 mol (689.8 g, 711.1 ml) trimethyl orthoformate then added dropwise within 8 h. During the dropwise addition of the trimethyl orthoformate 1.0 ml conc. HCl are added every 30 mins. After the reaction has ended, all volatile constituents are removed on the rotary evaporator under reduced pressure. The yellow, oily residue is distilled in fine vacuum (0.1 mbar). At 135 to 142° C. the product distils as a colourless, oily liquid (solidified melt Fp=42 C). Yield: 1001.0 g, 82% of theory.

EXAMPLE 4

9,10-dihydro-9-oxa-10-propoxyphosphaphenanthrene (6-propoxy-(6H)-dibenz [c,e][1,2]-oxaphosphorine) from DOP, Isopropanol and Triethyl Orthoformate 0.28 mol (59.5 g) DOP and 600 ml isopropanol are dissolved, 0.6 ml HCl are added and the mixture heated to 105° C. to reflux (slight excess pressure). After 1 h a further 0.15 ml conc. HCl are added and 0.55 mol (81.5 g, 92 ml) triethyl orthoformate then added dropwise within 3 h. During the dropwise addition of the triethyl orthoformate 0.15 ml conc. HCl are added every 15 mins. After the reaction has ended, all volatile constituents are removed on the rotary evaporator under reduced pressure. The yellow, oily residue is distilled in fine vacuum (0.1 mbar). At 142 to 145° C. the product distils as a colourless, oily liquid. Yield: 35.2 g, 78% of theory.

EXAMPLE 5

Oxidation of 9,10-dihydro-9-oxa-10-methoxyphospha-phenanthrene 100 mmol 9,10-dihydro-9-oxa-10-methoxyphospha-phenanthrene (6-methoxy-(6H)-dibenz[c,e] [1,2]-oxaphosphorine prepared as in Example 1 were heated to 160° C. in a flask with 2 mmol dimethyl sulphate accompanied by stirring and after 8 hours under these reaction conditions the rearrangement was complete. After cooling and washing with water, pure 9,10-dihydro-9-oxa-10-methylphosphaphenanthrene-10-oxide (6-methyl (6H)dibenz[c,e][1,2]-oxaphos-phorine-6-oxide) was obtained.

EXAMPLE 6

Oxidation of 9,10-dihydro-9-oxa-10-ethoxyphosphaphenanthrene 50 mmol 9,10-dihydro-9-oxa-10-ethoxyphosphaphenanthrene (6-ethoxy-(6H)-dibenz[c,e][1,2]-oxaphosphorine as prepared in accordance with Example 2 were heated to 160° C. in a flask with 2 mmol ethyl p-toluenesulphonate accompanied by stirring. After 8 hours under these reaction conditions the rearrangement was complete. After cooling and washing with water, pure 9,10-dihydro-9-oxa-10-ethylphosphaphenanthrene (6-ethyl (6H)dibenz[c,e][1,2]-oxaphosphorine-6-oxide) was obtained.

The reactions of Examples 5 and 6 can be carried out directly after the preparation of the educts according to Examples 1 and 2, i.e. without these being distilled in advance.

While several embodiments of the present invention have been shown and described, it is to be understood that many changes and modifications may be made thereunto without departing from the spirit and scope of the invention as defined in the appended claims.

What is claimed is:

1. A process for the preparation of 9,10-dihydro-9-oxa-10-organylphosphaphenanthrene-10-oxide and derivatives of Formula VIa or VIb comprising the steps of:

(a) reacting 9,10-dihydro-9-oxa-10-phospha-phenanthrene-10-oxide or a derivative of same according to Formula Ia or Ib,

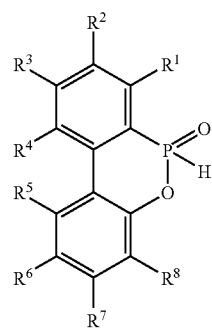

(Ia)

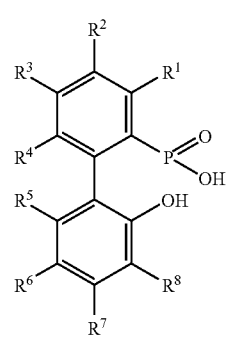

(Ib)

in which $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles, in the presence of at least one mono- or polyhydric alcohol of Formula IIIa

(IIIa)

in which $R^{11}$ is a mono- or polyvalent hydrocarbon group which optionally contains one or more heteroatoms selected from oxygen, nitrogen, sulphur, phosphorus, silicone and halogen, and y is 1 to 10, with at least one ortho ester of Formula II

(II)

in which $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, to form a first intermediate product, wherein the product obtained in step (a) has the Formula IVa or IVb

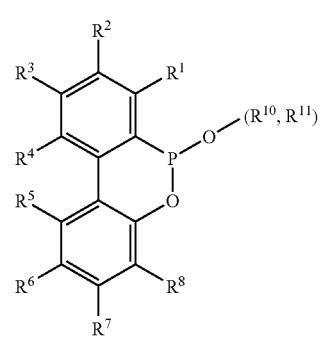

(IVa)

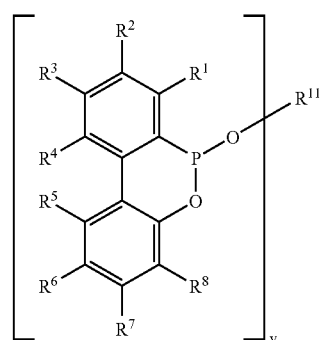

(IVb)

in which the radicals $R^1$ to $R^{11}$ and y have the meanings as stated above;

(b) transforming the first intermediate product from step (a) by addition of catalytic quantities of alkylation agent into 9,10-dihydro-9-oxa-10-organylphosphaphenanthrene-10-oxide or a derivative of same substituted on the phenyl groups, wherein the product obtained in step (b) has the Formula VIa or VIb

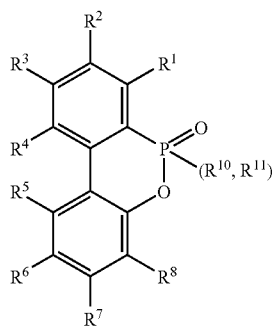

(VIa)

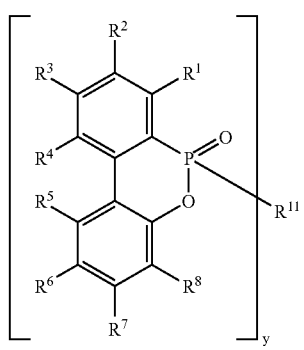

(VIb)

in which the radicals $R^1$ to $R^{11}$ have the same meanings as stated above.

2. A process for the production of 9,10-dihydro-9-oxa-10-organylphosphaphenanthrene-10-oxide and derivatives of Formula VIa or VIb comprising the steps of:

(a) reacting 9,10-dihydro-9-oxa-10-phospha-phenanthrene-10-oxide or a derivative of same according to Formula Ia or Ib,

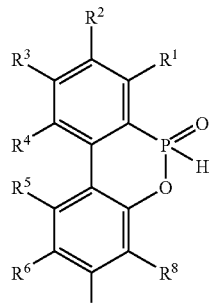

(Ia)

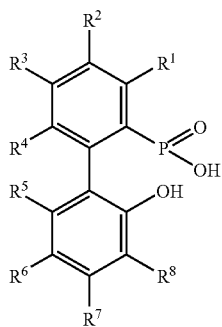

(Ib)

in which $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles, in the presence of at least one first mono- or polyhydric alcohol of Formula IIIa $$R^{11}(OH)_y \quad (IIIa)$$

in which $R^{11}$ is a mono- or polyvalent hydrocarbon group which optionally contains one or more heteroatoms selected from oxygen, nitrogen, sulphur, phosphorus, silicone and halogen, and y is 1 to 10, with at least one ortho ester of Formula II $$R^9C(OR^{10})_3 \quad (II)$$

in which $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, to form a first intermediate product, wherein the product obtained in step (a) has the Formula IVa or IVb

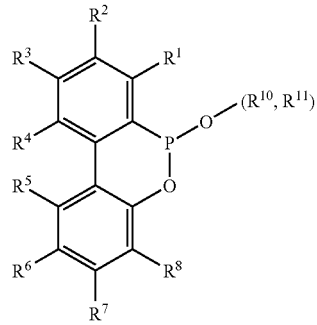

(IVa)

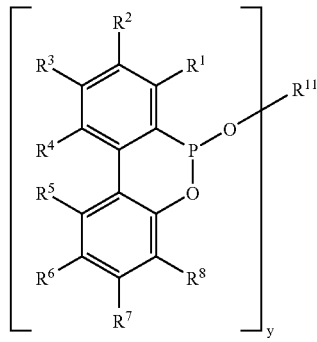

(IVb)

in which the radicals $R^1$ to $R^{11}$ and y have the meanings as stated above;

(b) reacting the first intermediate product from step (a) with at least one second mono- or polyhydric alcohol of Formula IIIb $$R^{12}(OH)_y \quad (IIIb)$$

in which $R^{12}$ is a mono- or polyvalent hydrocarbon group which optionally contains one or more heteroatoms selected from oxygen, nitrogen, sulphur, phosphorus, silicon and halogen, and y is 1 to 10, and the second alcohol is different from that used in step (a), to form a second intermediate product, wherein the product obtained in step (b) has the Formula Va or Vb,

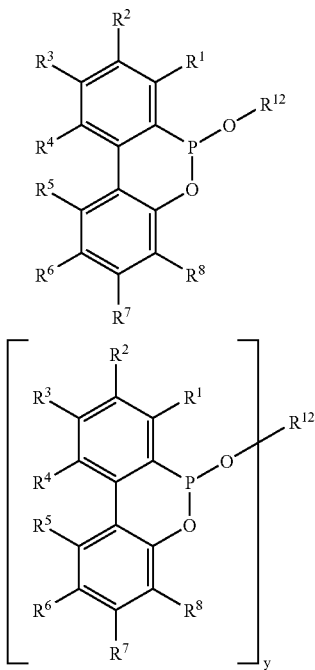

(Va)

(Vb)

in which the radicals $R^1$ to $R^{12}$ and y have the meanings as stated above;

(c) transforming the second intermediate product from step (b) by addition of catalytic quantities of alkylation agent into 9,10-dihydro-9-oxa-10-organylphosphaphen-anthrene-10-oxide or a derivative of same substituted on the phenyl groups, wherein the product obtained in step (c) has the Formula VIa or VIb

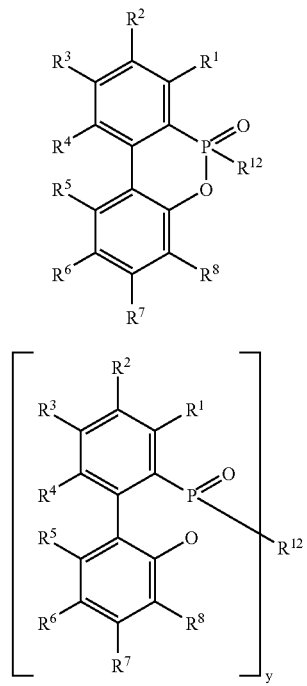

(VIa)

(VIb)

in which the radicals $R^1$ to $R^{12}$ have the same meanings as stated above.

3. The process according to claim 1, wherein in step (a) a 9,10-dihydro-9-oxa-10-phosphaphenanthrene-10-oxide derivative of Formula Ia or Ib

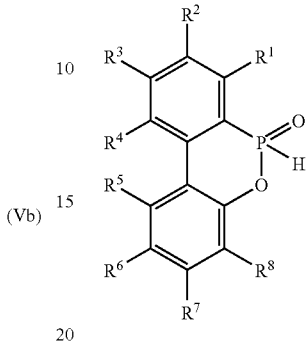

is used in which $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles.

4. The process according to claim 1, wherein in step (a) an ortho ester of Formula II

$$R^9(OR^{10})_3 \quad (II)$$

is used in which $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen.

5. The process according to claim 1, wherein in step (a) an alcohol of Formula IIIa

$$R^{11}(OH)_y \quad (IIIa)$$

is used in which $R^{11}$ is a mono- or polyvalent hydrocarbon group which optionally contains one or more heteroatoms selected from oxygen, nitrogen, sulphur, phosphorus, silicon and halogen, and y is 1 to 10.

6. The process according to claim 5, wherein y is 1, 2, 3 or 4.

7. The process according to claim 2, wherein in step (b) an alcohol according to Formula IIIb

$$R^{12}(OH)_y \quad (IIIb)$$

is used in which $R^{12}$ is a mono- or polyvalent hydrocarbon group which optionally contains one or more heteroatoms selected from oxygen, nitrogen, sulphur, phosphorus, silicon and halogen, and y is 1 to 10, and the alcohol is different from that used in step (a).

8. The process according to claim 7 wherein y is 1, 2, 3 or 4.

9. The process according to claim 7, wherein y is 1 for the alcohols used in each of the steps (a) and (b).

10. The process according to claim 7, wherein y=1 for the alcohol used in step (a) and y=2 to 4 for the alcohol used in step (b).

11. The process according to claim 5, wherein y=2 to 4 for the alcohol used in step (a).

12. The process according to claim 7, wherein y is 2 to 4 for the alcohols used in each of the steps (a) and (b).

13. The process according to claim 7, wherein y=2 to 4 for the alcohol used in step (a) and y=1 for the alcohol used in step (b).

14. The process according to claim 1, wherein the product obtained in step (a) has the Formula IVa or IVb

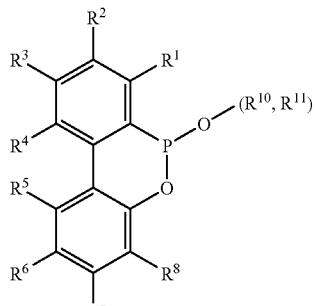

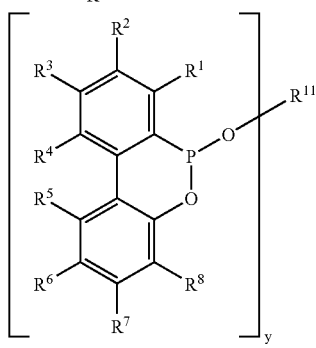

in which the radicals $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles, $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, $R^{11}$ is a mono- or polyvalent hydrocarbon group which optionally contains one or more heteroatoms selected from oxygen, nitrogen, sulphur, phosphorus, silicon and halogen, and y is 1 to 10.

15. The process according to claim 2, wherein the product obtained in step (b) has the Formula Va or Vb

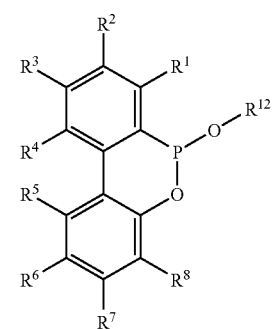

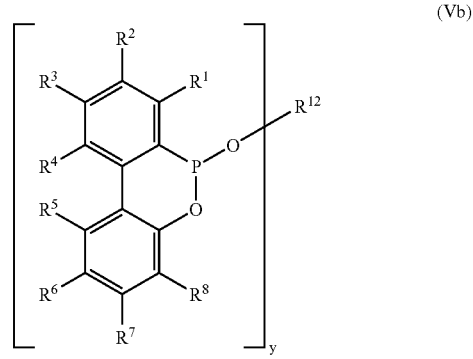

in which the radicals $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles, $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, $R^{11}$ is a mono- or polyvalent hydrocarbon group which optionally contains one or more heteroatoms selected from oxygen, nitrogen, sulphur, phosphorus, silicon and halogen, and $R^{12}$ is a mono- or polyvalent hydrocarbon group which optionally contains one or more heteroatoms selected from oxygen, nitrogen, sulphur, phosphorus, silicon and halogen, and y is 1 to 10.

16. The process according to claim 1, wherein 9,10-dihydro-9-oxa-10-phosphaphenanthrene-10-oxide is used in step (a).

17. The process according to claim 5, wherein an orthoformic acid ester selected from the group consisting of trimethyl orthoformate, triethyl orthoformate and triallyl orthoformate is used as ortho ester.

18. The process according to claim 17, wherein the monohydric alcohol (y=1) is selected from the group consisting of methanol, ethanol and isopropanol.

19. The process according to claim 17, wherein the polyhydric alcohol (y=2 to 4) is selected from the group consisting of a diol, glycol, polyglycol, trihydric alcohol and tetrahydric alcohol.

20. The process according to claim 19, wherein the polyhydric alcohol is selected from the group consisting of ethylene glycol, glycerol and pentaerythritol.

21. The process according to claim 2, wherein the catalyst in step (c) is selected from esters of sulphuric acid and esters of sulphonic acid.

22. The process according to claim 2, wherein the product obtained in step (c) has the Formula VIa or VIb

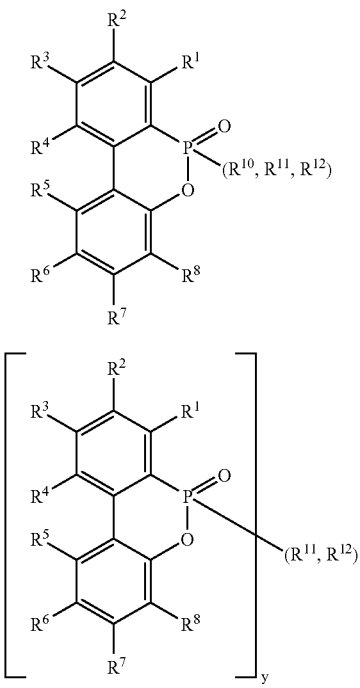

(VIa)

(VIb)

in which the radicals $R^1$ to $R^8$, independently of each other, are a hydrogen atom, halogen atom or a hydrocarbon group, the hydrocarbon groups optionally containing one or more heteroatoms selected from oxygen, nitrogen, sulphur, phosphorus, silicon and halogen, and two or more radicals $R^1$ to $R^8$ being optionally linked with formation of one or more cycles, $R^9$ is a hydrogen atom or a hydrocarbon group and the radicals $R^{10}$ are the same or different hydrocarbon groups which optionally contain one or more heteroatoms selected from oxygen, nitrogen, sulphur, phosphorus, silicon and halogen, $R^{11}$ is a mono- or polyvalent hydrocarbon group which optionally contains one or more heteroatoms selected from oxygen, nitrogen, sulphur, phosphorus, silicon and halogen, and $R^{12}$ is a mono- or polyvalent hydrocarbon group which optionally contains one or more heteroatoms selected from oxygen, nitrogen, sulphur, phosphorus, silicon and halogen, and y is 1 to 10.

23. The process according to claim 2, wherein a catalyst selected from the group consisting of Lewis acids and Brönsted acids is used in step (a) or (b).

24. The process according to claim 23, wherein the catalyst is selected from hydrogen halides and organic sulphonic acids.

25. The process according to claim 24, wherein the catalyst is hydrochloric acid or p-toluenesulphonic acid.

26. The process according to claim 23, wherein excess alcohol is removed and the catalyst used in step (a) or (b) is recovered.

27. The process according to claim 2, wherein reaction steps (a) to (c) are carried out in a reaction vessel.

* * * * *